(12) United States Patent
Kustra et al.

(10) Patent No.: US 10,695,130 B2
(45) Date of Patent: Jun. 30, 2020

(54) DOSE PLANNING SYSTEM

(71) Applicant: KONINKLIJKE PHILIPS N.V., Eindhoven (NL)

(72) Inventors: Jacek Lukasz Kustra, Eindhoven (NL); Guillaume Leopold Theodorus Frederik Hautvast, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 248 days.

(21) Appl. No.: 15/572,840

(22) PCT Filed: Jun. 10, 2016

(86) PCT No.: PCT/EP2016/063336
§ 371 (c)(1),
(2) Date: Nov. 9, 2017

(87) PCT Pub. No.: WO2016/198626
PCT Pub. Date: Dec. 15, 2016

(65) Prior Publication Data
US 2018/0153619 A1 Jun. 7, 2018

(30) Foreign Application Priority Data
Jun. 12, 2015 (EP) .................................. 15171904.4

(51) Int. Cl.
*A61B 34/10* (2016.01)
*A61N 5/10* (2006.01)
(Continued)

(52) U.S. Cl.
CPC ............ *A61B 34/10* (2016.02); *A61B 8/0841* (2013.01); *A61B 10/04* (2013.01); *A61B 18/02* (2013.01);
(Continued)

(58) Field of Classification Search
CPC .......... A61N 5/1031; A61N 2005/1087; A61N 5/1001; A61N 5/103; A61N 7/02;
(Continued)

(56) References Cited

U.S. PATENT DOCUMENTS

| 7,831,293 B2 | 11/2010 | Ellis et al. |
| 2003/0135115 A1 | 7/2003 | Burdette et al. |

(Continued)

FOREIGN PATENT DOCUMENTS

| WO | 2013028762 A1 | 2/2013 |
| WO | 2013140357 A1 | 9/2013 |

OTHER PUBLICATIONS

Shen, D. et al. "Optimized prostate biopsy via a statistical atlas of cancer spatial distribution" Medical Image Analysis 8 (2004) 139-150.
(Continued)

*Primary Examiner* — Christine H Matthews
*Assistant Examiner* — Joshua Daryl D Lannu
(74) *Attorney, Agent, or Firm* — Sherry Austin

(57) ABSTRACT

A dose planning system includes a biopsy map creation module configured for receiving biopsy information for an organ of interest regarding biopsy locations and tissue characteristics of tissue found at the biopsy locations and creating a spatially annotated biopsy map for the organ, by linking the spatial information on the biopsy locations to the tissue characteristics of tissue found at the corresponding biopsy locations. A probability map calculation module is configured for creating a tumor probability map by calculating a tumor probability for locations in the organ from which no biopsy was taken by using the tumor and/or tissue characteristics from the biopsy locations and a dose planning module configured for creating a dose plan based on the tumor probability map. The planning constraints are such
(Continued)

that on average a higher tumor probability results in a higher planned dose and a lower tumor probability results in a lower planned dose.

17 Claims, 3 Drawing Sheets

(51) Int. Cl.

| | | |
|---|---|---|
| A61B 18/02 | (2006.01) | |
| A61B 18/12 | (2006.01) | |
| A61B 18/20 | (2006.01) | |
| A61N 7/02 | (2006.01) | |
| A61B 8/08 | (2006.01) | |
| A61B 10/04 | (2006.01) | |
| G16H 20/10 | (2018.01) | |
| A61B 90/00 | (2016.01) | |
| A61B 18/14 | (2006.01) | |
| A61B 34/20 | (2016.01) | |
| A61B 17/34 | (2006.01) | |
| A61B 18/00 | (2006.01) | |

(52) U.S. Cl.
CPC .............. *A61B 18/12* (2013.01); *A61B 18/20* (2013.01); *A61N 5/1001* (2013.01); *A61N 5/103* (2013.01); *A61N 5/1031* (2013.01); *A61N 7/02* (2013.01); *G16H 20/10* (2018.01); *A61B 18/14* (2013.01); *A61B 2010/045* (2013.01); *A61B 2017/3413* (2013.01); *A61B 2018/00577* (2013.01); *A61B 2034/101* (2016.02); *A61B 2034/105* (2016.02); *A61B 2034/2063* (2016.02); *A61B 2090/364* (2016.02); *A61B 2090/365* (2016.02); *A61B 2090/378* (2016.02); *A61N 2005/1087* (2013.01)

(58) Field of Classification Search
CPC ... A61B 2090/365; A61B 18/02; A61B 18/20; A61B 18/12; A61B 10/04; A61B 8/0841; A61B 2018/00577; A61B 2017/3413; A61B 2010/045; A61B 18/14; A61B 2090/364; A61B 34/10; A61B 2034/101; A61B 2034/105; A61B 2034/2063; A61B 2090/378; G16H 20/10

See application file for complete search history.

(56) References Cited

U.S. PATENT DOCUMENTS

| | | |
|---|---|---|
| 2010/0303330 A1 | 12/2010 | Moriya |
| 2011/0125011 A1* | 5/2011 | Wieczorek ............. A61B 6/032 600/427 |
| 2011/0263922 A1 | 10/2011 | Dornberger et al. |
| 2013/0116548 A1* | 5/2013 | Kumar ................. A61B 8/0841 600/424 |
| 2013/0329973 A1* | 12/2013 | Cao ...................... A61B 5/0033 382/128 |

OTHER PUBLICATIONS

Menze, B.H. et al. "Image-based modeling of tumour growth in patients with glioma", Australasian Phyisical & Engineering Sciences in Medicine, Sep. 2016, vol. 39, Issue 3, pp. 601-613.
Workshop on Optimal control in image processing, Heidelberg University, Germany, May 31 & Jun. 1, 2010.
Gevertz, J.L. et al, "Simulating tumour growth in confined heterogeneous environments" Phys. Biol. 5 (2008) 036010.
Korporaal, J.G. et al., "The use of probability maps to deal with the uncertainties in prostate cancer delineation", Radiotherapy and Oncology, Elsevier, vol. 94, No. 2, Feb. 1, 2010, pp. 168-172.
Feleppa, E.J. et al., "Progress in characterizing arid imaging prostate tissues for guiding biopsies and planning and targeting treatment of prostate cancer", 2003 IEEE Ultrasonics Symposium-1018.
Montironi, R. et al., "Extent of cancer of less than 50% in any prostate needle biopsy core: how many millimeters are there", European Urology, vol. 61, Issue 1, Apr. 2012, pp. 751-756.

* cited by examiner

DOSE PLANNING SYSTEM

CROSS-REFERENCE TO PRIOR APPLICATIONS

This application is the U.S. National Phase application under 35 U.S.C. § 371 of International Application Serial No. PCT/EP2016/063336, filed on Jun. 10, 2016, which claims the benefit of European Patent Application No. 15171904.4, filed on Jun. 12, 2015. This application is hereby incorporated by reference herein.

FIELD OF THE INVENTION

The invention relates to a dose planning system for a therapeutic treatment of diseased tissue of an organ and more specifically the invention relates to a dose planning system for treatment in the field of oncology.

BACKGROUND OF THE INVENTION

Treatment of tumours in cancer patients can be performed using several approaches, ranging from minimally invasive approaches such as brachytherapy to surgical approaches where the full organ containing the tumour is removed. Less invasive, focal therapies are gaining popularity due to improvements in early detection and screening, and the potentially reduced side-effects.

The workflow from cancer diagnosis till treatment consists of several stages. A biopsy is usually performed during the diagnostic stage to assess the tumour type and provide a score on the cancer extent. The biopsy is usually taken at multiple locations, and a global score is generated. Several approaches are used to produce this global score:

1. millimeters of cancer per core
2. total millimeters of cancer among all cores
3. percentage of cancer per core
4. total percentage of cancer in the entire specimen
5. number of positive cores
6. fraction of positive cores (number of positive cores and total cores)

U.S. Pat. No. 7,831,293B2 describes a method of defining a biological target for treatment. This document describes a method, wherein a detectable marker is left at a biopsy location. This marker is used to correlate histopathological data with functional imaging. Because the data set used to produce a tumour treatment plan can distinguish and differentiate the specific pathology and tumour progression or aggressiveness of different regions of the target tissue, the treatment plan can be used to direct therapy to different regions of discrete biological target volume tissue at different intensities. The pathologically defined points for tumour are correlated to a functional study (e.g. MRSI, SPECT, PET or optical biopsy) such that positive findings on the functional image can serve as a known marker for known disease sites. If the functional study is able to detect these areas of heretofore occult tumour foci, then other areas showing activity on the functional study can be treated as representing additional occult tumour foci, and thereby used to define a biological target volume for treatment.

SUMMARY OF THE INVENTION

It is an object of the invention to improve treatment planning. This object is achieved by a dose planning system for a therapeutic treatment of diseased tissue of an organ of interest comprising a biopsy map creation module configured for receiving biopsy information for an organ of interest regarding biopsy locations and tissue characteristics of tissue found at the biopsy locations, wherein the biopsy map creation module is further configured for creating a spatially annotated biopsy map for the organ, by linking the spatial information on the biopsy locations to the tissue characteristics of tissue found at the corresponding biopsy locations and a probability map calculation module configured for creating a tumour probability map by calculating a tumour probability for locations in the organ from which no biopsy was taken by using the tumour and/or tissue characteristics from the biopsy locations and a dose planning module configured for creating a dose plan based on the tumour probability map, wherein planning constraints are such that for an area with an average higher tumour probability a higher planned dose is planned and for an area with an average lower tumour probability in a lower planned dose is planned.

Currently within radiation treatment two important challenges exist. The first is that precise delineation of tumour tissue may be complicated. A lot of variation exists between delineations made by different observers based on the medical images. Furthermore, determination of the correct dose may be challenging. It has been proposed to vary the dose within the tumour based on the tumour aggressiveness to increase tumour control probability and reduce side effects. However, this so-called dose painting by numbers approach always relies on (functional) imaging (e.g. PET, Diffusion Weighted MRI, Dynamic Contrast Enhanced MRI) of the tissue. It is an insight of the inventors that these imaging techniques only provide indirect measures of tumour probability and tumour aggressiveness. Therefore, by directly using the biopsy results to calculate a tumour probability map, which is in turn the input for a dose planning module, the treatment plan may be improved. The tumour probability map could be a map providing a spatial distribution of estimated chances of tumour presence. It could also provide a spatial distribution on expected tumour cell densities or aggressiveness levels (e.g. Gleason score in the case of prostate cancer).

According to embodiments of the invention, the dose planning system further comprises an image guided biopsy system configured for taking a biopsy from predetermined locations in the organ and further configured for providing at least spatial information on the biopsy locations to the biopsy map creation module. This embodiment is advantageous, because it could help to improve a tumour treatment workflow. Targeted biopsies could be performed and based on a histopathological analysis of the biopsies, directly a biopsy map could be created, which could then be used to calculate the probability map and the dose plan. This plan could then directly be used for treatment. Image guidance could for example be provided by means of ultrasound or magnetic resonance imaging.

According to a further embodiment of the invention, the image guided biopsy system comprises a photonic needle. Automatic analysis of the spectrum retrieved by the photonic needle would further speed up the diagnosis to treatment process.

According to a further embodiment of the invention, the image guided biopsy system comprises a registration module configured to register an image of the organ acquired by the ultrasound system with an image of the organ acquired by a second medical image system, wherein the biopsy locations are at least partly determined based on the image acquired by the second medical image system. This embodiment is advantageous, because although ultrasound may be very good for image guidance, in certain situations like e.g. for prostate cancer, ultrasound may not be the imaging modality of choice to determine locations containing suspicious tissue. In these situations suspicious tissue locations may be determined based on images acquired with a different imaging modality, e.g. like MRI, PET, SPECT, (contrast enhanced) CT. After image registration the suspicious locations found by images acquired by the second medical image system could be translated to the ultrasound coordinate system.

The dose planning system could be configured for creating a dose plan for one out of radiotherapy, proton therapy, cryotherapy, radiofrequency ablation, laser ablation or high intensity focused ultrasound treatment.

These and other aspects of the invention will be apparent from and elucidated with reference to the embodiments described hereinafter.

DETAILED DESCRIPTION OF THE INVENTION

Figure 1:
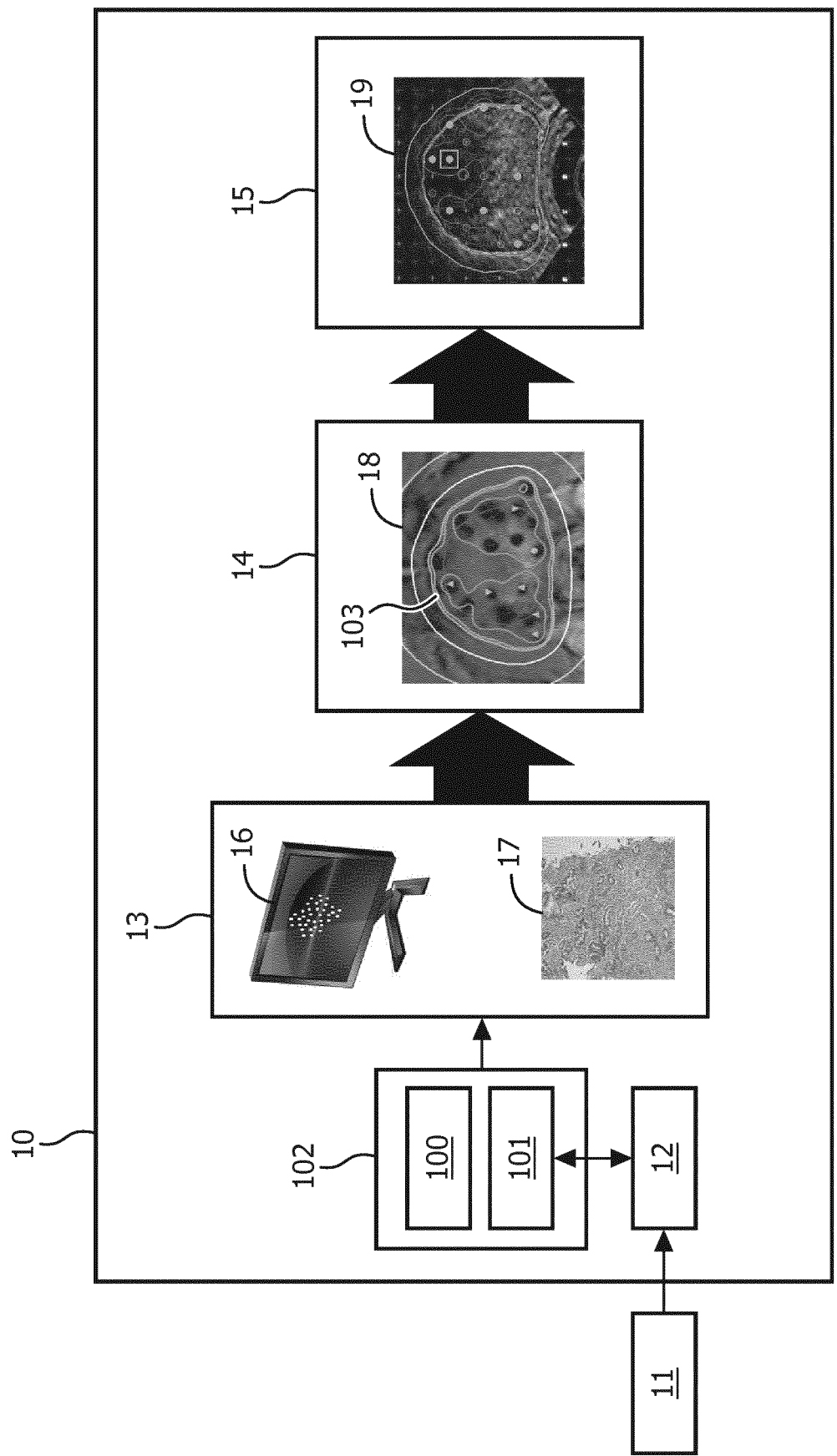
FIG. 1 shows a dose planning system according to the invention.

FIG. 1 shows a dose planning system 10 according to the invention. The dose planning system comprises a biopsy map creation module 13, a probability map calculation module 14 and a dose planning module 15. A dose planning workflow using the invention could start with the acquisition 11 of images of an organ of interest based on which the suspicious locations within the organ could be identified. Also non-suspicious locations could be identified. These images could for example be magnetic resonance (MR) images. The MR images could be provided to registration module 12. During a biopsy procedure, image guided biopsy system 102 could acquire ultrasound images for biopsy guidance by means of ultrasound system 101. At least one of the ultrasound images is provided to the registration module 12. The registration module then registers the ultrasound image with the MR image, such that the identified suspicious and non-suspicious locations of the organ can be translated to the imaging coordinate system of the ultrasound system 101. An operator of the system could then guide a photonic needle 100 to the identified locations to perform histopathological analysis on the tissue 17.

Alternatively a biopsy can be taken and sent to the pathology department for analysis. The tissue analysis results in tissue characteristics like tumour cell density, percentage of tumour cells, tumour aggressiveness etc. The tissue characteristics determined from the biopsy tissue 17 and biopsy locations 16 are provided to the biopsy map creation module 13, which creates a biopsy map by linking the biopsy locations to the corresponding tissue characteristics.

The biopsy map serves as an input for the probability map calculation module 14, which uses it to calculate a tumour probability map 18. Here line 103 surrounds an area wherein the tumour probability exceeds a certain threshold. The probability map calculation module 14 could be configured for creating the tumour probability map 18 based on interpolation or a tumour shape model. Interpolation could be advantageous, since this method does not require prior knowledge on tumour shape.

A tumour shape model could make use of available statistical information on tumour spread in relation to e.g tumour cell density, tumour aggressiveness, DNA mutations, DNA expression levels, protein levels found in the biopsy material. Tumour shape models are for example known from Shen et al. *Optimized prostate biopsy via a statistical atlas of cancer spatial distribution* Medical Image Analysis 8 (2004) 139-150. In their approach, they experimentally generate a global probability cloud for finding a positive biopsy finding and use it for optimal needle placement. The key item here of use for the present invention, is the probability distribution, which can be used for modeling the tumour probability map.

Other examples of references describing tumour distributions which could be used as an input to generate a tumour probability map are Menze et al. *Image-based modeling of tumour growth in patients with glioma* Optimal control in image processing, Springer, Heidelberg/Germany, 2011. hal-00825866 and Gevertz et al. *Simulating tumour growth in confined heterogeneous environments* Phys. Biol. 5 (2008) 036010. Also further data could be collected on the likelihood of tumour presence on a certain location given a positive or negative biopsy sample at another location.

Figure 2:
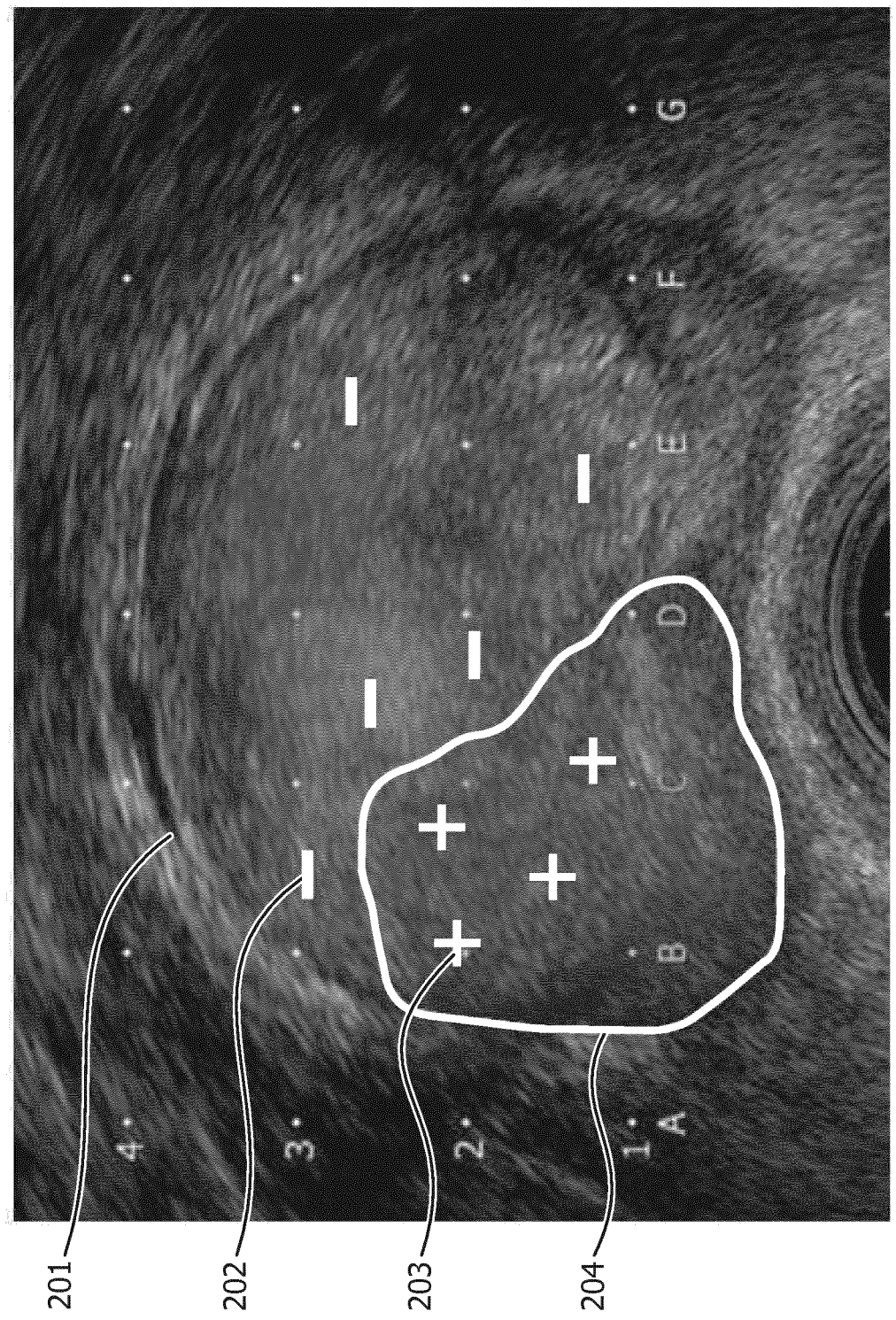
FIG. 2 shows an example of a tumour probability map.

FIG. 2 shows an example of a tumour probability map. FIG. 2 shows an ultrasound image of a prostate 204. Locations where a biopsy has been taken, but no tumour was found are indicated by means of a "−" sign 202. Locations where a biopsy has been taken and where tumour was found in the biopsy sample are indicated with a "+" sign 203. The tumour probability decreases from positions 203 towards line 204, which is an iso-line indicating a certain value for the tumour probability, e.g. 95%.

Figure 3:
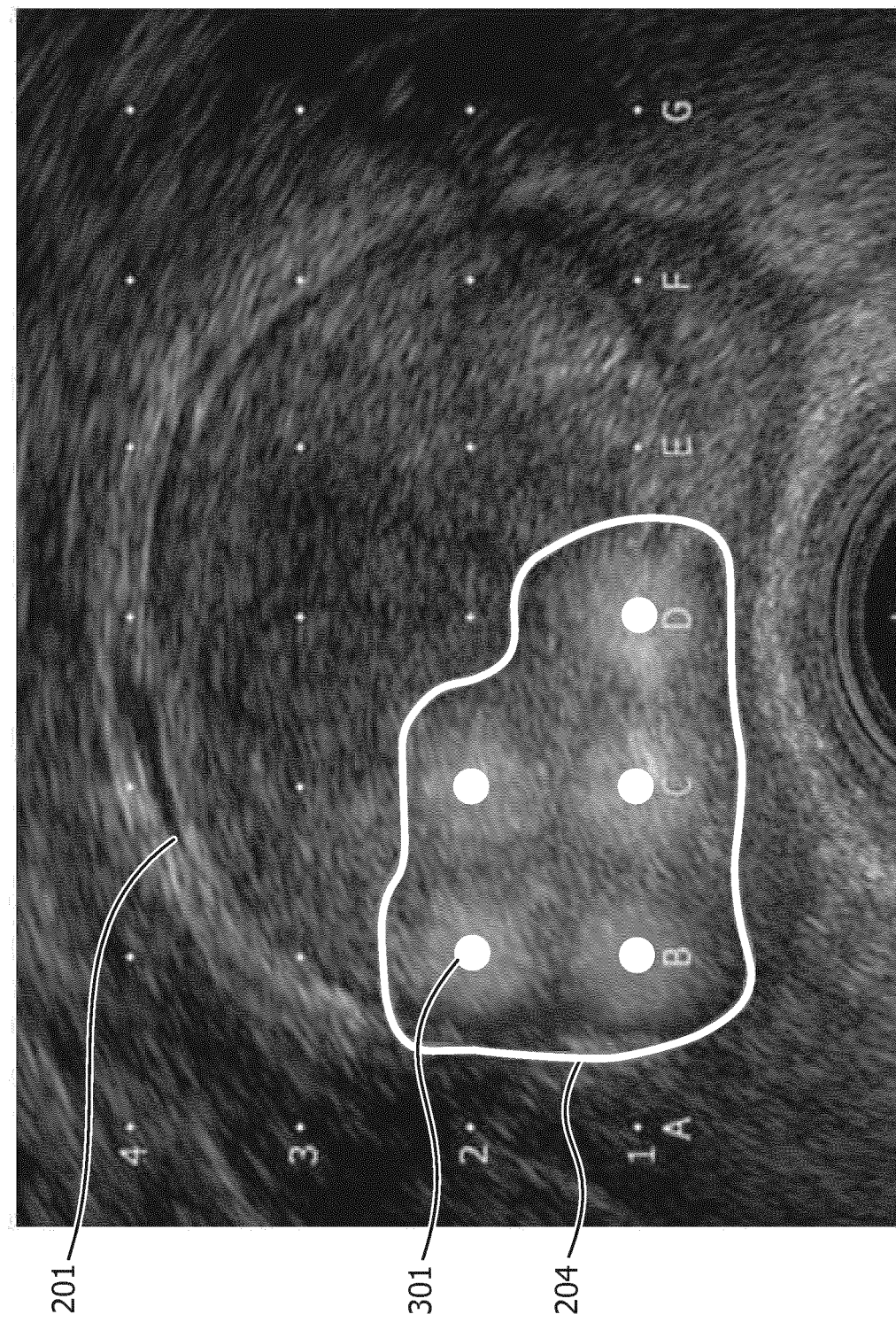
FIG. 3 shows a dose plan corresponding to the tumour probability map of FIG. 2.

The tumour probability map is provided to the dose planning module 15, which creates a dose plan 19 based on the tumour probability map. FIG. 3 shows a dose plan corresponding to the tumour probability map of FIG. 2. The area surrounded by iso-line 204 is considered as gross tumour volume (GTV) and the treatment is planned as such.

Alternatively, the dose planning module could for example create the dose plan based on the tumour probability map by means of radiobiological models. These models typically take into account tumour cell density, but they could also take into account tumour aggressiveness or the level of hypoxia, which affects at least radiotherapeutic outcome and may be determined based on e.g. HIF-1 levels. These values could be obtained from the biopsy samples and used in the tumour probability map. The radiation dose could also be determined based on interpolation. Alternatively, one could also choose to apply a boost dose to a region with high (e.g. >95%) tumour probability and apply standard dose to regions with low to intermediate tumour probability (e.g. 5-95%). The dose planning module could be also configured to use dose constraints for an organ at risk located near the organ to be treated. However, other examples are possible and the invention is not restricted to the examples disclosed.

Whilst the invention has been illustrated and described in detail in the drawings and foregoing description, such illustrations and description are to be considered illustrative or exemplary and not restrictive; the invention is not limited to the disclosed embodiments and can be used for dose planning in the field of disease treatment.

The invention claimed is:

1. A dose planning system for a therapeutic treatment of diseased tissue of an organ of interest, the system comprising a non-transitory computer-readable medium carrying software configured to control a computer processor to:
   receive biopsy information for an organ of interest regarding biopsy locations and tissue characteristics of tissue found at the biopsy locations,
   create a spatially annotated biopsy map for the organ, by linking spatial information on the biopsy locations to the tissue characteristics of tissue found at the corresponding biopsy locations,
   create a tumor probability map by calculating a tumor probability for locations in the organ from which no biopsy was taken by using the tumor characteristics and/or the tissue characteristics from the biopsy locations, and
   create a dose plan based on the tumor probability map, wherein planning constraints are such that for an area with an average higher tumor probability a higher dose is planned and for an area with an average lower tumor probability a lower dose is planned.

2. The dose planning system as claimed in claim 1, wherein the tumor probability map indicates a spatial distribution of one of estimated chances of tumor presence, expected tumor cell densities or tumor aggressiveness level.

3. The dose planning system as claimed in claim 1, further comprising an image guided biopsy system configured for taking a biopsy from the biopsy locations in the organ and further configured for providing the biopsy information.

4. The dose planning system as claimed in claim 3, wherein the image guided biopsy system comprises a photonic needle, wherein the photonic needle is configured for providing the biopsy information.

5. The dose planning system as claimed in claim 3, wherein the image guided biopsy system comprises an ultrasound system for image guidance during the biopsy.

6. The dose planning system as claimed in claim 5, further comprising a registration module configured to register an image of the organ acquired by the ultrasound system with an earlier image of the organ acquired by a second imaging modality.

7. The dose planning system as claimed in claim 1 wherein a dose planning is configured for creating a dose plan for at least one of a group of treatments, comprising: brachytherapy, proton therapy, cryotherapy, radiofrequency ablation, laser ablation and high intensity focused ultrasound treatment.

8. The dose planning system as claimed in claim 1, wherein the tumor probability map is created based on interpolation of the tumor and/or tissue characteristics between the biopsy locations or based on a tumor shape model using the tumor and/or tissue characteristics as an input.

9. The dose planning system as claimed in claim 1, wherein the tumor characteristics are at least one of a group of characteristics, comprising: cell density, size of the tumor in a biopsy sample, percentage of the tumor per biopsy sample or a measure related to tumor aggressiveness.

10. The dose planning system as claimed in claim 1, wherein the dose plan uses dose constraints for an organ at risk located near the organ to be treated.

11. A dose planning method for a therapeutic treatment of diseased tissue of an organ of interest comprising:
   receiving biopsy information for an organ of interest regarding biopsy locations and tumor and/or tissue characteristics of a tumor and/or tissue found at the biopsy locations;
   creating a spatially annotated biopsy map for the organ by linking spatial information on the biopsy locations to the tumor and/or tissue characteristics of the tumor and/or tissue found at the corresponding biopsy locations;
   creating a tumor probability map by calculating a tumor probability for locations in the organ from which no biopsy was taken by using the tumor and/or tissue characteristics from the biopsy locations; and
   creating a dose plan based on the tumor probability map, wherein planning constraints are such that for an area with an average higher tumor probability a higher dose is planned and for an area with an average lower tumor probability a lower dose is planned.

12. A non-transitory computer-readable medium carrying software configured to control a computer processor to perform the method as claimed in claim 11.

13. A dose planning system for a therapeutic treatment of disease of an organ of interest, the system comprising:
   an image guided biopsy system configured for taking a biopsy from predetermined locations in the organ and providing at least spatial information on biopsy locations; and
   one or more computer processors configured to perform the method of claim 11.

14. A dose planning system for a therapeutic treatment of diseased tissue of an organ of interest, the system comprising:
   an image guided biopsy system configured for taking a biopsy from predetermined locations in the organ and providing spatial information on biopsy locations; and
   one or more processors configured to:
      receive the biopsy locations from the image guided therapy system,
      receive tumor and/or tissue characteristics of tumors and/or tissue found at the biopsy locations,
      create a spatially annotated biopsy map for the organ by linking the spatial information on the biopsy locations to the tumor and/or tissue characteristics at the corresponding biopsy locations,
      create a tumor probability map by calculating a tumor probability for locations in the organ from which no biopsy was taken by using the tumor and/or tissue characteristics from the biopsy locations, and
      create a dose plan based on the tumor probability map using planning constraints such that for an area with an average higher tumor probability a higher planned dose is planned and for an area with an average lower tumor probability a lower planned dose is planned.

15. The dose planning system as claimed in claim 14, wherein the tumor probability map is a spatial distribution of one of estimated chances of tumor presence, expected tumor cell densities, or tumor aggressiveness level.

16. The dose planning system as claimed in claim 14, wherein creating the probability map is based on interpolation of the tumor and/or tissue characteristics between the biopsy locations or based on a tumor shape model using the tumor and/or tissue characteristics.

17. The dose planning system as claimed in claim 14, wherein dose planning constraints minimize dose to an organ at risk located near the organ to be treated.

* * * * *